(12) United States Patent
Schwerin

(10) Patent No.: US 8,838,232 B1
(45) Date of Patent: Sep. 16, 2014

(54) MULTIFUNCTION ELECTRIC RAZOR HAVING AN ELECTRICAL STIMULATOR

(76) Inventor: Thomas Edward Schwerin, Flagstaff, AZ (US)

(*) Notice: Subject to any disclaimer, the term of this patent is extended or adjusted under 35 U.S.C. 154(b) by 0 days.

(21) Appl. No.: 13/459,026

(22) Filed: Apr. 27, 2012

Related U.S. Application Data

(60) Provisional application No. 61/609,814, filed on Mar. 12, 2012.

(51) Int. Cl.
*A61N 1/00* (2006.01)
*A61N 1/36* (2006.01)

(52) U.S. Cl.
CPC .................................. *A61N 1/36* (2013.01)
USPC .............................................................. 607/2

(58) Field of Classification Search
CPC ........ B26B 19/14; B26B 19/38; B26B 19/42; B26B 21/48; B26B 21/40; B26B 21/00; H03F 21/00; A61N 1/36021; A61N 1/36
USPC .............................................................. 607/2
See application file for complete search history.

(56) References Cited

U.S. PATENT DOCUMENTS

| | | | |
|---|---|---|---|
| 3,197,612 A | 7/1965 | Reich | |
| 3,316,633 A * | 5/1967 | Tapper | 30/34.2 |
| 5,119,558 A * | 6/1992 | van Erp et al. | 30/43.6 |
| 5,301,425 A * | 4/1994 | Ferraro | 30/42 |
| 5,394,611 A * | 3/1995 | Okabe et al. | 30/43.6 |
| 5,687,481 A * | 11/1997 | De Boer et al. | 30/43.1 |
| 5,692,303 A * | 12/1997 | Garenfeld et al. | 30/43.9 |
| 6,014,918 A * | 1/2000 | Orloff | 83/13 |
| 6,481,104 B1 | 11/2002 | Parker et al. | |
| 6,502,309 B2 * | 1/2003 | De Vries et al. | 30/34.2 |
| 6,544,259 B1 | 4/2003 | Tsaliovich | |
| 2004/0171970 A1 | 9/2004 | Schleuniger et al. | |
| 2004/0230258 A1 | 11/2004 | Altshuler et al. | |
| 2009/0000123 A1 | 1/2009 | Trezon | |
| 2009/0287208 A1 | 11/2009 | Rosemberg | |
| 2010/0024615 A1 | 2/2010 | Rebaudieres et al. | |
| 2011/0256249 A1 | 10/2011 | Campbell et al. | |

FOREIGN PATENT DOCUMENTS

GB 1120349 7/1968

* cited by examiner

*Primary Examiner* — Christopher D Koharski
*Assistant Examiner* — Roland Dinga
(74) *Attorney, Agent, or Firm* — Invention To Patent Services; Alex R. Hobson

(57) ABSTRACT

An electric razor having an electrical stimulator is provided. The razor may be used to both shave and tighten muscles, especially in the face while shaving. The article may be configured as a hand held electric razor comprising a plurality of cutting features that may be configured as electrodes. The cutting features may be configured in any suitable way, including discrete substantially circular cutting features, such as a three blade razor. A user mode feature may be configured on the razor or control device to allow a user to use the razor alone, the stimulator alone, or the razor and stimulator in combination.

20 Claims, 9 Drawing Sheets

US 8,838,232 B1

MULTIFUNCTION ELECTRIC RAZOR HAVING AN ELECTRICAL STIMULATOR

CROSS REFERENCE TO RELATED APPLICATIONS

This application claims the benefit of U.S. Provisional Patent Application No. 61/609,814, filed on Mar. 12, 2012, which is incorporated herein by reference in its entirety.

BACKGROUND OF THE INVENTION

1. Field of the Invention

The present invention relates to electric razors having an electrical stimulation feature that makes hair stand up for a closer shave. The razor may be deactivated and the article may be used as a hand held electrical stimulator.

2. Background

Most men shave on a regular basis and there are a number of choices in shaving devices that men can currently select from, including a razor and an electric razor. Women however, for the purposes of shaving their legs, do not typically use an electric razor and instead shave with a razor while in the shower or bathtub, which can be very inconvenient. There are many types of electric razors available having rotating or reciprocating blades. Usually the blades are configured beneath a screen whereby hair protrudes through and is cut by the blades.

As a person ages, the muscles in the face lose their tightness and elasticity causing the face to droop or sag, making a person appear older. Electrical stimulation of muscles can tighten muscles and firm up the face, thereby preventing or reversing sagging. Electrical stimulation of tissue may have any number of other advantages and benefits including, but not limited to, acne prevention, muscle toning, wound healing acceleration, collagen restoration and the like.

SUMMARY OF THE INVENTION

The invention is directed to an electric razor having an electrical stimulator. The razor may be used to both shave and tighten muscles, especially in the face, while shaving. The article may be configured as a hand held electric razor comprising a plurality of cutting features. The cutting features may be configured in any suitable way, including discrete substantially circular cutting features. In an exemplary embodiment, the electric razor comprises three discrete cutting features that are substantially circular in shape, herein referred to as a three blade razor. The blades may be configured to reciprocate or rotate about an axis. A cutting feature may further comprise a screen that covers the blades and has openings to allow hair to protrude therethrough. A cutting feature, blade and/or screens may be configured to move or flex to conform to the curvature of the face. The screens may be electrically isolated and/or insulated from the rest of the razor and may be connected electrically to an electrode of the electrical stimulator.

The electrical stimulator comprises an electrical power source that provides an electrical charge to an activating electrode, and a separate return electrode. The electrical stimulator may also comprise a controller that controls the electrical stimulating signal frequency and voltage. In an exemplary embodiment, the electrical stimulating signal voltage is sufficient to cause the muscles around the hair follicles to contract, thereby making the hair stand up. Any suitable electrical stimulating signal voltage may be used including, but not limited to, more than about 70 V, more than about 90 V, more than about 100 V, more than about 110 V, more than 180 V, more than 200 V, or no more than about 70 V, no more than about 90 V, no more than about 110 V, no more than 180 V, no more than 200 V, and any range between and including the voltage values provided. Any suitable electrical stimulating signal frequency may be used including, but not limited to, more than about 0.5 Hz, more than about 1 Hz, more than about 2 Hz, more than about 3 Hz, more than about 5 Hz, more than about 10 Hz, more than about 20 Hz, more than 50 Hz, more than 70 Hz, more than 100 Hz, or no more than about 1 Hz, no more than about 2 Hz, no more than about 3 Hz, no more than about 5 Hz, no more than about 10 Hz, no more than about 20 Hz, no more than 50 Hz, no more than 70 Hz, no more than 100 Hz and any range between and including the frequency values provided. A lower frequency may be used to stimulate deeper muscle responses. Lower frequencies may tend to allow the stimulating signal, or electrical current to move deeper into a user's skin, muscle and tissue. In a preferred embodiment the electrical stimulating signal is set to approximately 10 Hz and approximately 35 volts.

The electrical stimulating signal may have any suitable signal profile including, but not limited to, an oscillating profile, a periodic profile, a saw-tooth profile, combinations thereof, and the like. In addition, the electrical stimulating signal may reverse poles, whereby an activating electrode becomes a return electrode and a return electrode becomes an activating electrode.

The razor described herein may further comprise a user stimulator setting feature, whereby a user may change the amount of electrical stimulation by adjusting the voltage and/or the frequency of the electrical stimulating signal. The amount of voltage required to effectively transfer the charge to a user's skin may depend on any number of factors, including the conductivity of the user skin, the presences of any lotion, oils or other substances on a user's skin, the relative humidity, and the like. A user may choose to increase or decrease the electrical stimulating signal voltage, as a function of these variables. A higher voltage may be used for shaving and a lower voltage may be selected when the razor is used in a stimulator mode, as will be described further herein. In an exemplary embodiment, a first electrode receives a first electrical stimulating signal, and a second electrode receives a second electrical stimulating signal that is different from the first electrical stimulating signal. For example, a first electrode may receive a first electrical stimulating signal that is suitable for getting the hair to stand up, and a second electrode may receive a second electrical stimulating signal that is suitable for a second purpose such as toning the face muscles, or preventing acne and the like.

The activating electrode may be any suitable skin contact feature, such as a screen or an electrically conductive contact configured for contact with the skin, such as during shaving. Any number and configuration of electrodes may be configured on the shaving surface of the razor as described herein. In one embodiment, a screen is an activating electrode and in another embodiment a plurality of screens are activating electrodes. In one embodiment, a screen is a return electrode and in another embodiment a plurality of screens are return electrodes. In yet another embodiment, a first screen is an activating electrode and a second screen is a return electrode. In another embodiment, an electrode, such as a return electrode is configured on the body of the razor, in a location to make contact with a user's hand when they hold and use the electric razor described herein.

An electrode, such as a skin contact feature, may be configured in any suitable way. For example, a skin contact electrode may be configured around one or more of the cutting features. In one embodiment, a skin contact electrode substantially surrounds each cutting feature, and in another embodiment, a skin contact electrode substantially surrounds a plurality of cutting features. In an exemplary embodiment, a plurality of screens are configured as activating electrodes and a skin contact feature is configured as a return electrode and configured on the shaving surface.

The activating and return electrodes may be configured to provide any suitable electrical flow distance, or the distance electrical current has to travel from an activating electrode to a return electrode. In some embodiments, an activating and return electrode are configured on a shaving surface of a razor, as described herein, therein providing a short electrical flow distance such as, but not limited to, no more than about 10 cm, no more than about 5 cm, no more than about 3 cm, no more than about 2 cm, no more than about 1 cm, no more than about 5 mm, no more than about 2 mm, no more than about 1 mm, and any range between and including the distance values provided. In another embodiment, wherein one electrode is configured on the body of the razor for contact with a user hand, and the opposing electrode is configured as a screen on the shaving surface, the electrical flow distance is the distance from the contact point on the user's face to the electrode contact on the user's hand. In this configuration, the electrical flow distance is no more than about two meters, no more than 1 meter, no more than about three quarters of a meter, no more than about half a meter and any range between and including the distances provided.

An electrode, such as a screen or skin contact feature, may comprise a conductive or electrically insulating coating over a portion of the surface of the electrode. In addition, a coating on an electrode may impart some surface roughness to the electrode surface. In some cases a roughened surface may provide for more uniform transfer of charges to the user's skin.

An electrode, such as a screen or skin contact feature may be electrically conductive or comprise electrically conductive material. In one embodiment, the electrode consists essentially of metal. The screen may be aluminum, copper or any other suitable metal or combination thereof. In one embodiment, the electrode is comprised of metal wire that is configured around at least one cutting feature. In another embodiment, the electrode comprises a metal foil.

Any suitable type of power supply may be used to power or charge the razor, as described herein, including, but not limited to, a battery, a rechargeable battery, an electrical input from a power cord, an electrical coupling line that extends from the razor to a power supply and/or controller device, and the like. The power supply should be selected to provide a suitable voltage to the electrical stimulator and power the razor. The razor may be used in areas that may be wet, and measures should be taken with the design of the power supply to ensure the safety of the user.

The razor, as described herein, may further comprise a user mode feature, whereby a user may turn off the razor and use the article as an electrical stimulator only, or in stimulator mode, or may turn off the electrical stimulator and use the razor as a razor only, or in razor mode. In stimulator mode, the razor blades are turned off, and a user may press the razor against their face, or any other part of their body, and move it slowly to stimulate the muscles and thereby tighten the muscles, accelerate healing, prevent acne, restore collagen and the like. Periodic use of the razor as described herein, in the stimulator mode may reduce sagging and dropping of the face, and thereby make someone appear younger. Likewise, a user may choose to use the razor in razor mode and turn off the electrical stimulator. In a "combination mode", both the razor and electrical stimulator are activated during use. The razor, as described herein, may be used on the face, legs or any other location of the body, and may be used as a razor and stimulator or as either independently.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
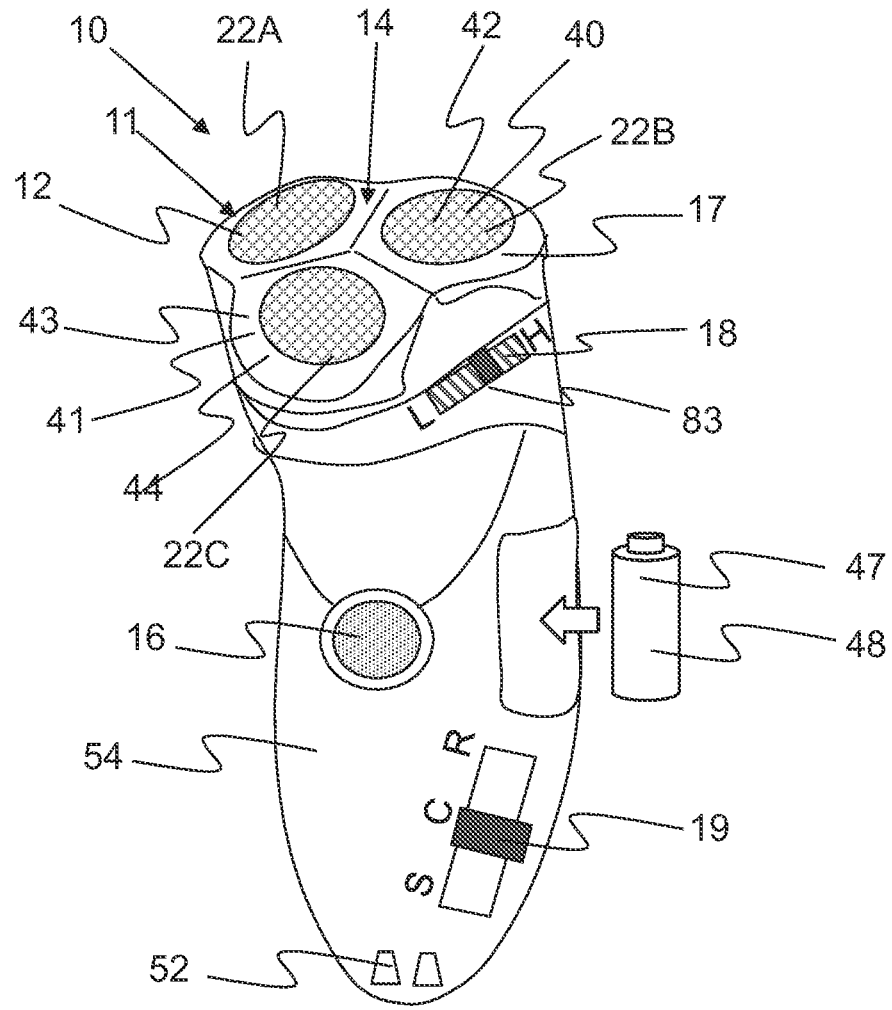

FIG. 1 shows an isometric view of an exemplary razor with an electrical stimulator comprising, three cutting features.

Figure 2:
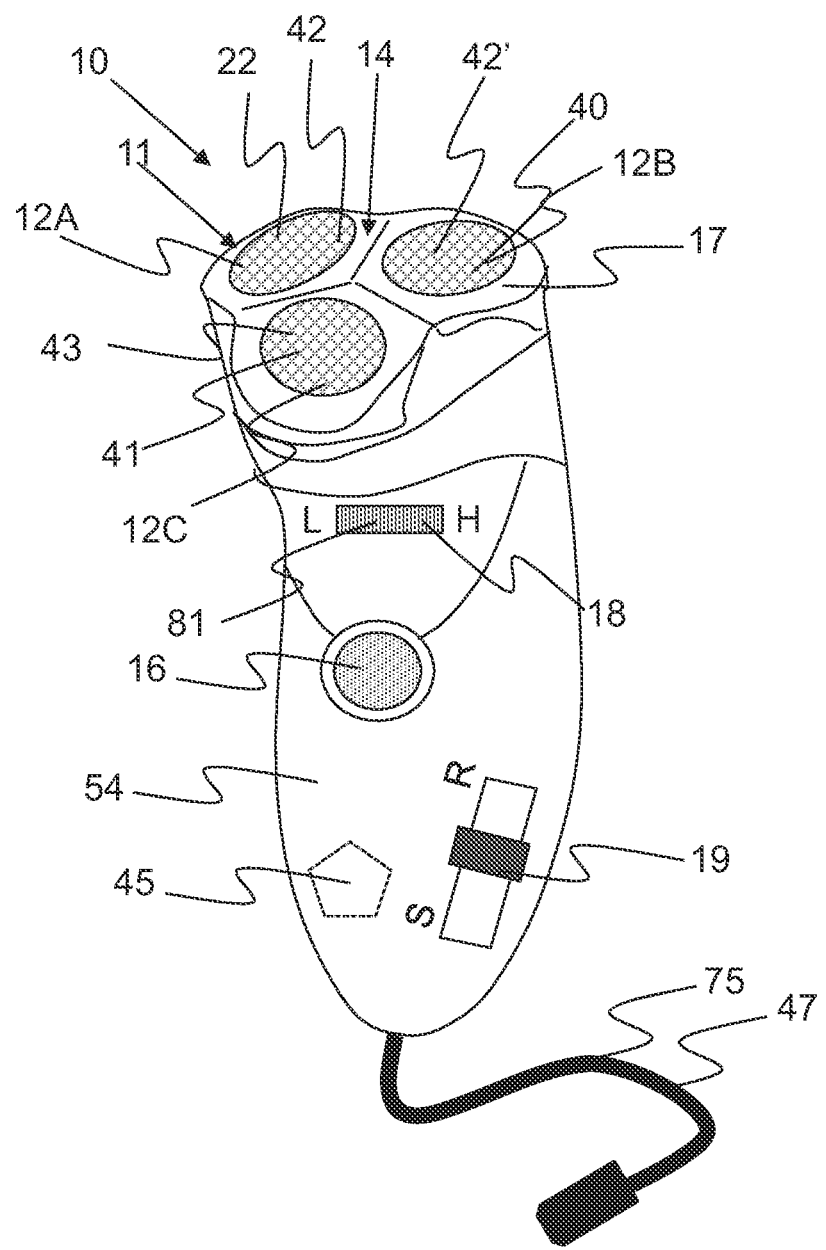

FIG. 2 shows an isometric view of an exemplary razor with an electrical stimulator comprising three cutting features.

Figure 3:
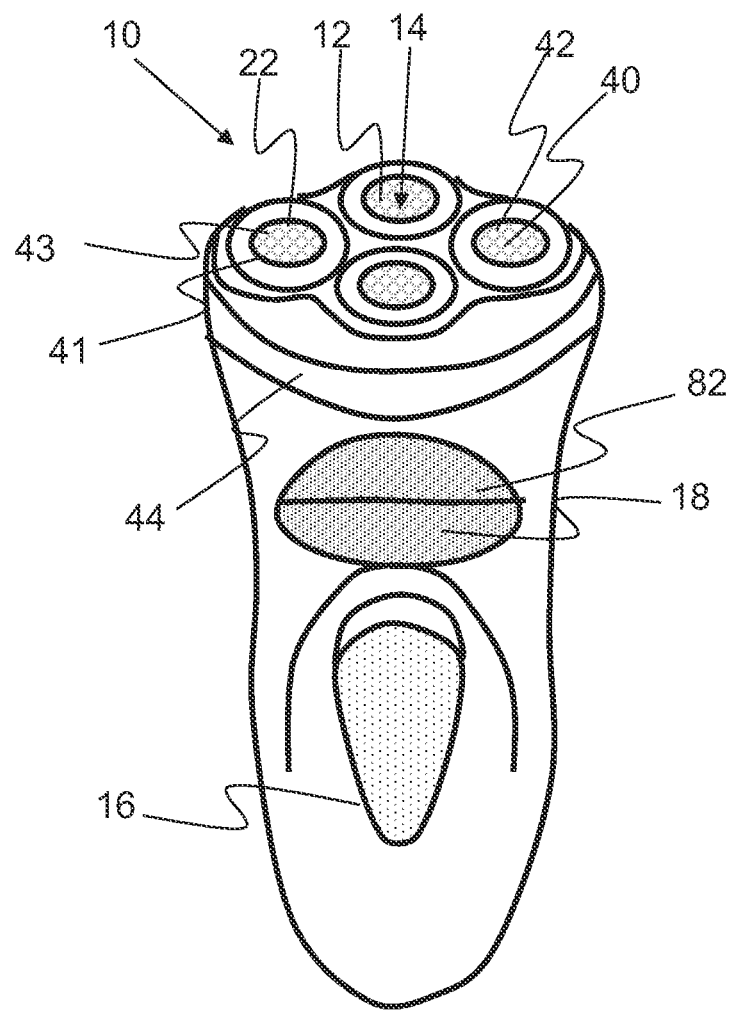

FIG. 3 shows an isometric view of an exemplary razor comprising four cutting features and an electrical stimulator.

Figure 4:
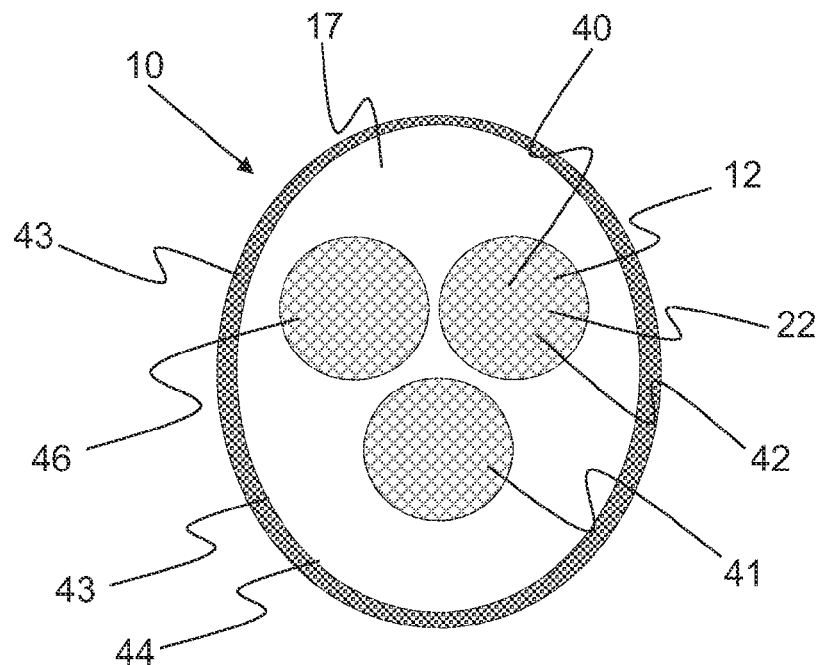

FIG. 4 shows a top down view of an exemplary razor with three cutting features on the shaving surface, and a skin contact feature surrounding the three cutting features.

Figure 5:
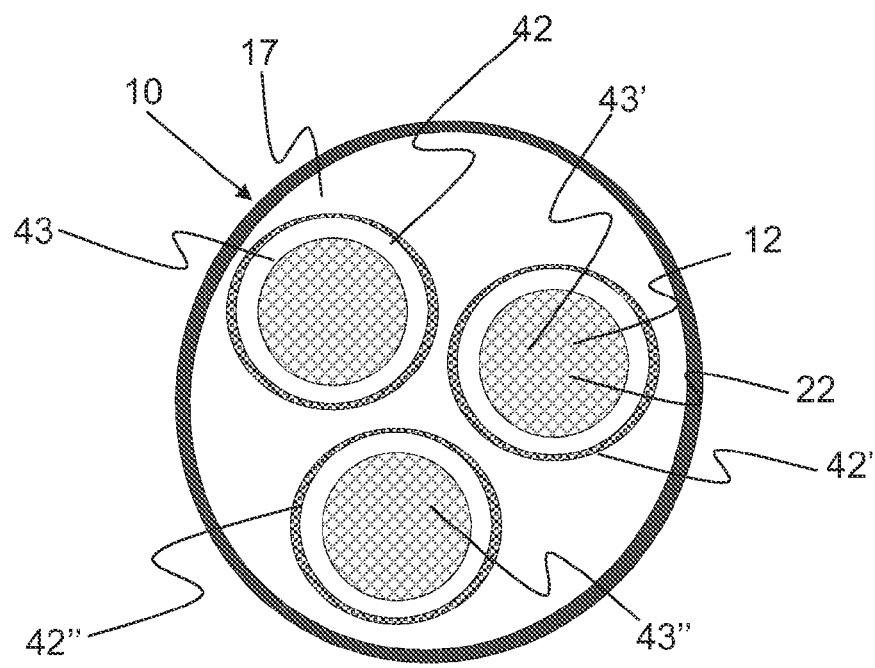

FIG. 5 shows a top down view of an exemplary razor with three cutting features on the shaving surface, and a skin contact feature surrounding each of the three cutting features.

Figure 6:
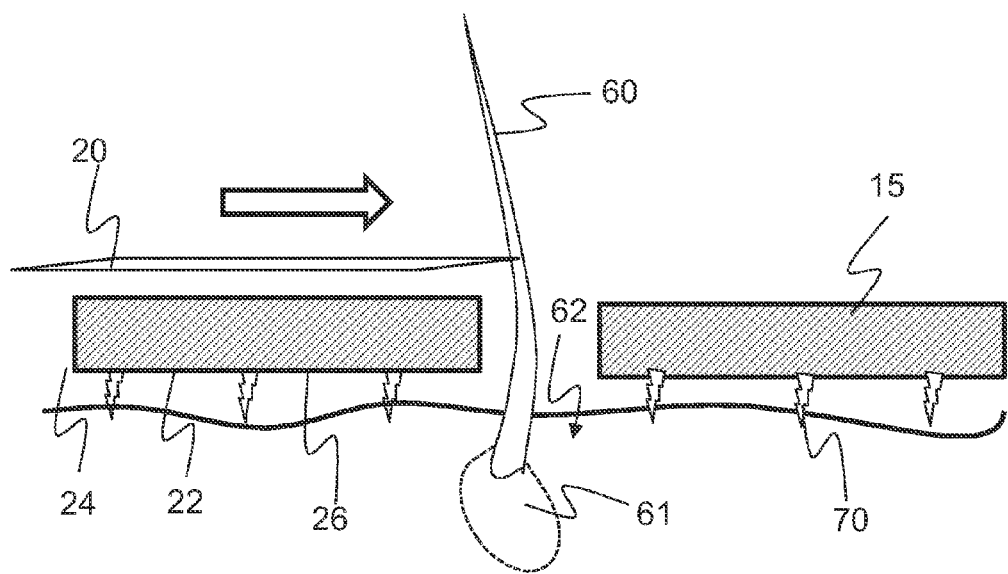

FIG. 6 shows a cross sectional side view of a screen, and a hair extending through a gap in the screen.

Figure 7:
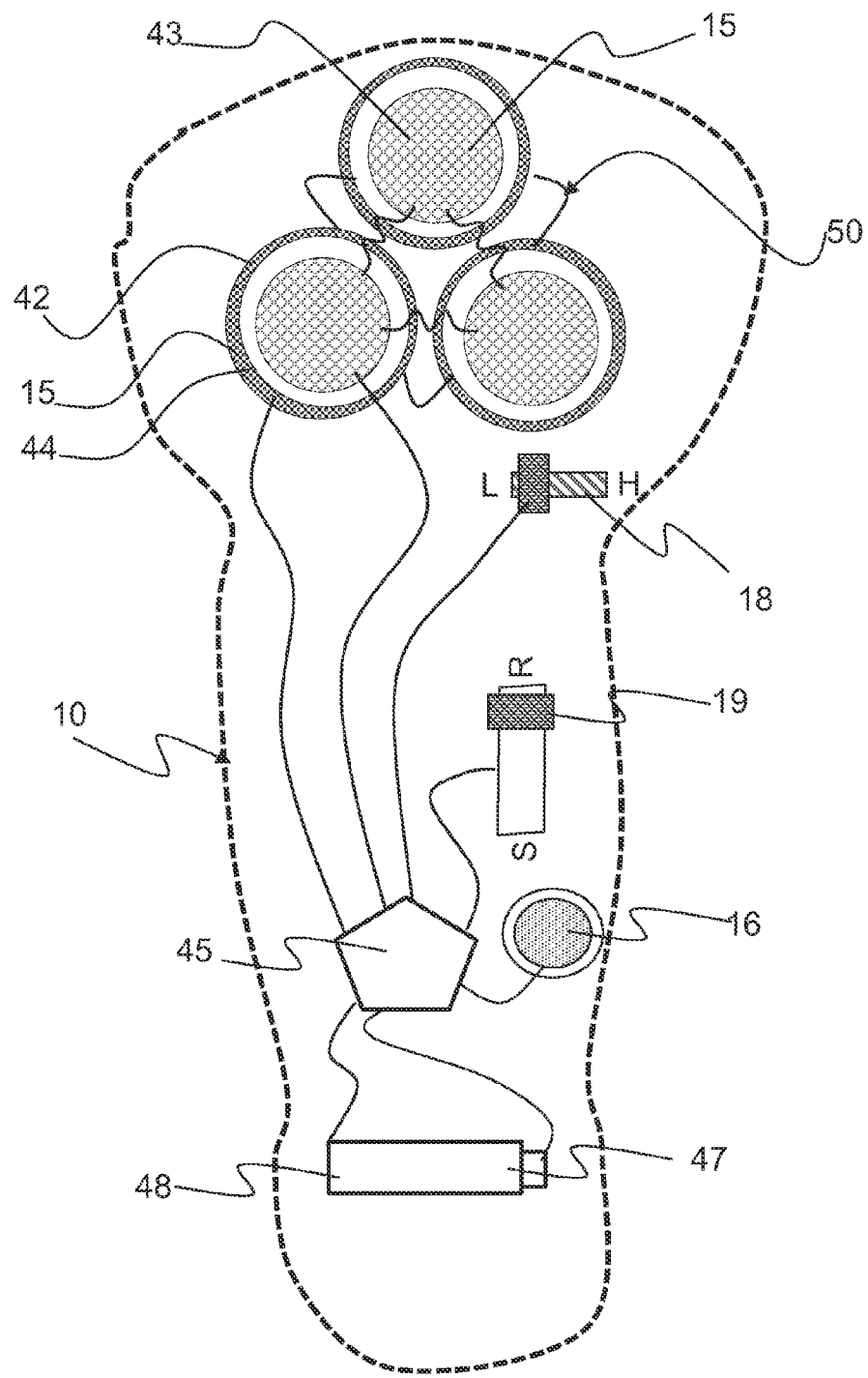

FIG. 7 shows a diagram of an exemplary control system of a razor as described herein, comprising a controller electrically connected with electrodes, power supply, and user control features.

Figure 8:
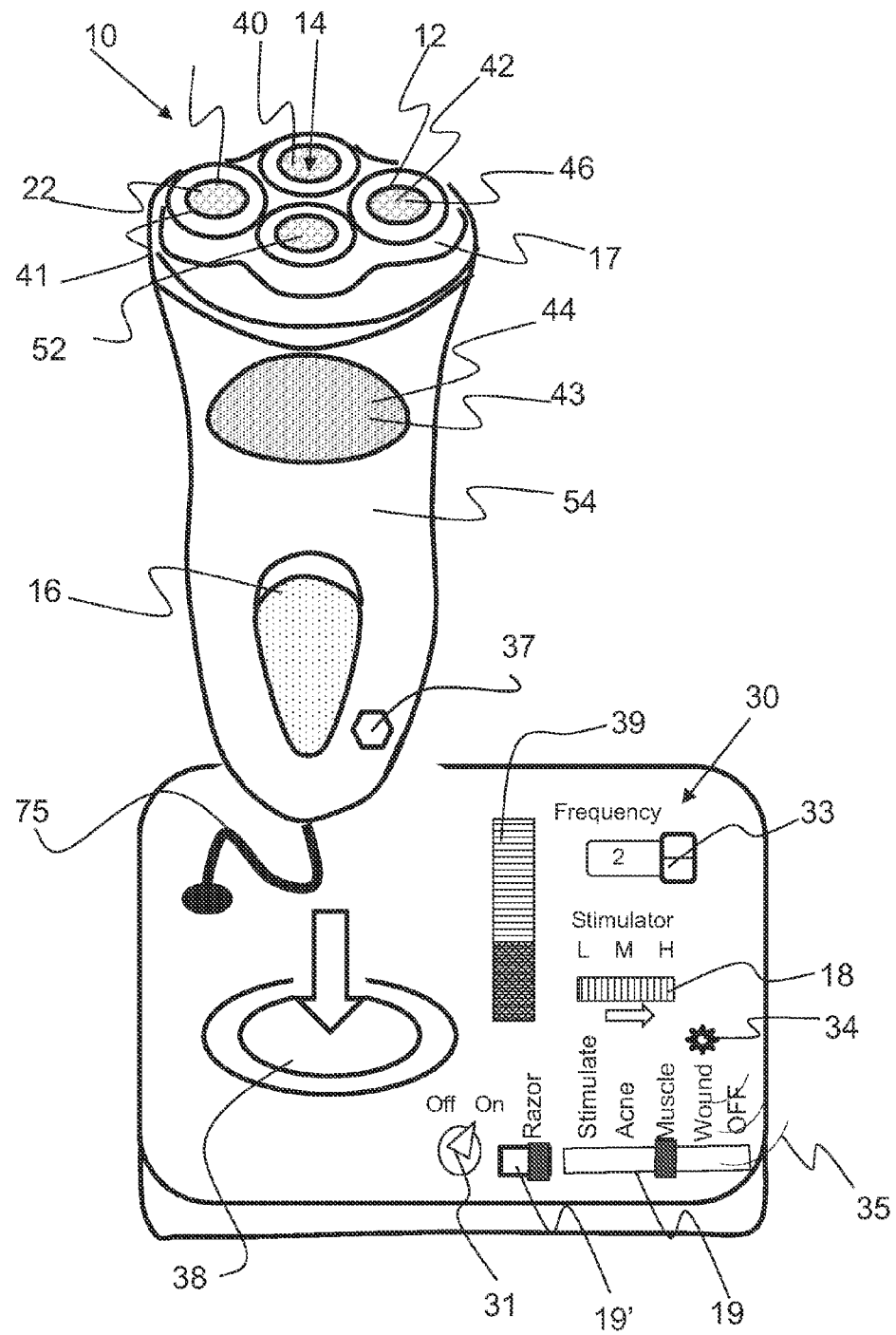

FIG. 8 shows an isometric view of an exemplary multifunction electric razor stationed in a control device.

Figure 9:
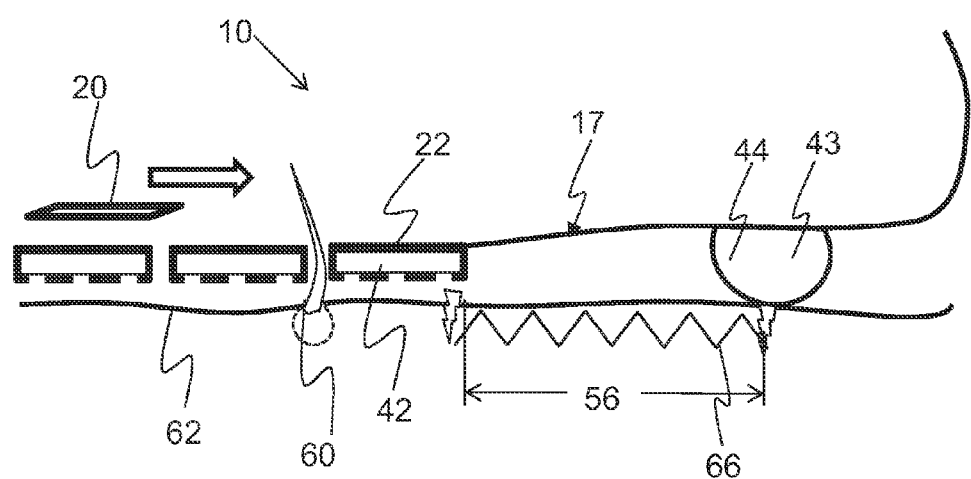

FIG. 9 shows a cross-sectional side view of a screen type activating electrode, and a skin contact feature type return electrode, and the electrical flow distance therebetween.

FIG. 10A-10D show electrical stimulating signal profiles.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but as a representative basis for teaching one skilled in the art to employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown if FIG. 1 an exemplary three blade razor 11 type electric razor 10 comprises three cutting features 12 configured on a cutting surface 17. The cutting features depicted are discrete cutting features that have a substantially round shape. As depicted in FIG. 1, the cutting feature comprises blades (not shown) configured behind the screens 22A, 22B and 22C. In this embodiment, the three screens 22(A-C) are activating electrodes 42, and a skin contact feature 44 acts as a return electrode. The skin contact feature 44 surrounds the cutting features and may be configured as any portion of the shaving surface 17. The electrical stimulator 14, of the exemplary razor 10 depicted in FIG. 1, charges the screens 22, and in use, the charge would pass through a person's skin to a return electrode 43, or the skin contact feature 44. The exemplary razor depicted in FIG. 1 further comprises an on/off button 16, a stimulator setting feature 18, and a user mode feature 19. The stimulator setting feature 18, shown in FIG. 1, is a voltage setting feature 83 having discrete settings including, low (L) and high (H). Any number of discrete settings may be configured into a stimulator setting feature 18. In addition, a stimulator setting feature may have a continuous variable setting, such as a dial as shown in FIG. 2. The user mode feature 19, depicted in FIG. 1, provides a setting for shaving or activating the razor (R), a setting for the electrical stimulator (S), and a setting for combination mode (C). As depicted in FIG. 1, the user mode feature switch is set to C, a combination mode, that activates both the razor and the electrical stimulator. Any suitable setting device configuration and type may be used, and any suitable labeling including, but not limited to, words, letters or symbols may be used to indicate the setting position. The exemplary razor depicted in FIG. 1 comprises a battery 48 type power source 47. The battery is shown outside of the razor and an arrow indicates the location of the battery housing within the razor. Any suitable type and number of batteries may be used, including rechargeable batteries. The razor, as described herein, may comprise electrical charging contacts 52 for charging the batteries.

The exemplary three razor type 11, electric razor 10 depicted in FIG. 2 comprises three cutting features 12A, 12B and 12C configured on a cutting surface 17. In this embodiment, the two screens are the activating electrodes 42, 42', and the third screen is the return electrode 43. Any configuration of electrodes may be used. In some embodiments, not all of the screens are electrodes. It may be desirable to use only selected screens for electrodes because of their configuration on the shaving surface. One or more screens may be an activating electrode or a return electrode. Furthermore, in some embodiments, an electrode may switch from an activating electrode to a return electrode. For example, the controller 45, may control the electrical stimulating signal to the electrodes and may alternate the signal, such that electrodes reverse polarity. The electrodes may reverse polarity in a periodic manner, an oscillating manner, a saw-tooth manner, or at a given frequency, or they may change as a function of some sensory input, such as resistance, or voltage. The exemplary razor depicted in FIG. 2 comprises a coupling cord 75 type power source 47. The coupling cord may be configured to be plugged into a controller device 30 (not shown), or any other suitable power conversion device that can regulate the power to the razor to ensure it is functional and safe.

The exemplary razor shown in FIG. 3 comprises four cutting features 12. Any suitable number of cutting features may be configured on a razor, as described herein, including, but not limited to, one, more than one, two or more, three or more, four or more, five or more, six or more and any number between and including the quantity of cutting features provided. The stimulator setting feature 18, in this embodiment, is a toggle switch 82, whereby a user my toggle the switch up to increase the charge of the activating electrodes or toggle it down to reduce the charge.

An electrode may comprises any portion of a cutting feature, such as a screen, or ring around a cutting feature, as well as any skin contact feature. As used herein, coupled to an electrode, means that the item described is electrically connected with the controller to act as an electrode.

As shown in FIG. 6, a screen 22 may be an electrode 15 and transfer charge 70 from the electrode to a user's skin 62. A hair 60 is depicted, in FIG. 6, extending through an open space in the screen 22. A blade 20 is depicted as being configured behind the screen and rotating, as indicated by the arrow, to cut the hair.

The diagram depicted in FIG. 7 shows a controller 45, electrically connected to a power source 47, a user mode feature 19, a stimulator setting feature 18, an on/off button 16, an activating electrode 42, and a return electrode 43. The controller 45 may control some or all the functions of the razor, such as the voltage level and the frequency of the stimulating signal to the electrode(s). A separate controller, in a controller device 30, shown in FIG. 8, may control some of the feature of the razor and a controller in the razor may control other functions, of the razor, or communicate with the controller in the control device. The controller may reverse the polarity of the electrodes periodically, in an oscillating profile, a periodic profile, a saw-tooth profile, combinations thereof, and the like. The controller may comprise a microprocessor. As shown in FIG. 7, one or more electrodes may be electrically connected by an electrical connector 50. As shown in FIG. 7, skin contact features surround the screens and act as the activating electrodes. As depicted in FIG. 7, the three screens are electrically connected, and the three surrounding skin contact features are electrically connected, as indicated by the connecting lines.

As shown in FIG. 8, the multifunction electric razor 10, as described herein, may be configured with a controller device 30. The razor 10, may be configured to be plugged into, or be connected by a coupling cord 75 to the controller device 30. In another embodiment, as shown in FIG. 8, the razor 10, is configured to be charged by the controller device, whereby the controller device comprises a charging feature 38 and the razor may be couple thereto, as indicated by the downward arrow. A remote razor 10, such as a razor not physically coupled to a control device 30, would provide more freedom of movement and convenience to a user. Any suitable type or combination of power supply may be used to power and/or charge the razor. The control device 30 may comprise a stimulating setting feature 18 and/or a user mode feature 19 and 19', as shown in FIG. 8. As shown in FIG. 8, the user mode feature 19' provides a means for a user to turn the razor shaving function on or off, whereas the user mode feature 19 provides a means for a user to select a specific stimulating mode, or turn off the stimulator function.

A stimulator indicator 39 may display the actual or relative voltage value. As shown in FIG. 8, the stimulator indicator is a column of lights, such as LED lights, whereby more lights are illuminated in an ascending manner as the voltage is increased. In addition, the lights at the bottom of the column may be green, the lights toward the middle of the column may be yellow and the lights at the top of the column may be red, thereby further indicating a relative stimulation voltage level. Any suitable type of indicator may be used, such as a digital display that shows the actual voltage value. Numbers, text or other characters may be used in conjunction with a stimulator indicator to represent stimulator voltage levels, or relative levels. The control device may further comprise a frequency setting feature 33 and an on/off switch 31. In some embodiments, a razor 10 may be configured to work with a control device 30 remotely, whereby the controller device comprises a signal output device 34, and the razor comprises a signal receiver 37 as shown in FIG. 8. In this embodiment, changes to the setting on the control device 30, would change the output of the razor 10 through transmission of a wireless signal 35 from the control device to the razor. As shown in FIG. 8, input and control information set on the control device 30 may be transferred to the electric razor 10 through the coupling cord 75.

As shown in FIG. 8, a skin contact feature 44 is configured on the body of the razor 54 and acts as a return electrode. A user would make skin contact with the return electrode 43 when holding the electric razor, as described herein. The electric flow distance in this example would be the distance from a user's hand, where it touches the skin contact feature 44, to the place on the persons skin where they press the shaving surface 17 and contact an activating electrode 42.

Electrical stimulation may have any number of other advantages and benefits including, but not limited to, acne prevention, muscle toning, wound healing acceleration, collagen restoration and the like. The frequency and voltage of the electrical stimulating signal, as well as the electrical flow distance, may be adjusted for any of the other purposes described herein. The razor may comprise set points for these purposes that the user may simply select using a user mode feature 19, as shown in FIG. 8. For example, on a razor 10 or on a control device 30, a user switch may have any of the following set points, including razor, stimulate, combination (for shaving and stimulating), acne prevention, wound healing, muscle toning, and collagen restoration, and the like, as shown in FIG. 8. The specific text, characters or symbols used to represent these or other set points may be any suitable type, including pictures or figures. The controller may set the stimulating frequency and voltage as a function of the user mode input setting. For example, the frequency may be set to a relatively low frequency of 2 HZ and the voltage may be set to a relatively high voltage of 110 V, when the muscle toning set point is selected, as shown in FIG. 8.

In other embodiments, a user may manually control the electrical stimulating signal frequency and voltage. A user may, for example, set a specific voltage and frequency for acne prevention, whereby the stimulating signal effectively causes a hair follicle to contract, thereby expelling any fluids, such as sebum, that may become infected or irritated and lead to pimples or acne. In another embodiment, the voltage and frequency may be set to provide wound healing, whereby a reverse polarity electrical stimulating signal may be used. In yet another embodiment, the electrical stimulating signal may be set to provide muscle toning, whereby the frequency may be reduced to approximately 10 Hz, and the voltage may be set to approximately 50 V, for example. The razor, as described herein, may be used both as a razor and as an electrical stimulator. As shown in FIG. 8, a user mode feature 19' allows a user to turn the razor on or off, and user mode feature 19 allows a user to select a stimulating mode. With separate user input mode features for the razor and stimulator, a user can use the razor in combination with any of the stimulating modes, or alone. A razor, as described herein, may be configured to provide two or more different stimulating signals. Furthermore, the razor may be configured to reverse the polarity of the electrodes.

As described herein, the multifunction electric razor may be configured with a first electrode that receives a first stimulator signal, and a second electrode that receives a second stimulator signal. One signal may be suitable for making a hair stand up, while the other signal is suitable for some other purpose including, but not limited to, acne prevention, muscle toning, wound healing, and the like. In some embodiments, the multifunction electric razor may be used in a stimulator mode for one of the purposes described herein.

An electrical flow distance 56 of an electrical stimulating signal 66 is shown in the cross sectional view of FIG. 9 as the distance between a screen 22 type activating electrode 42 and a skin contact feature 44 type return electrode 43. The electrical flow distance may be configured to be any suitable distance and may be on the order of millimeters or on the order of fractions of a meter.

Figure 10A:
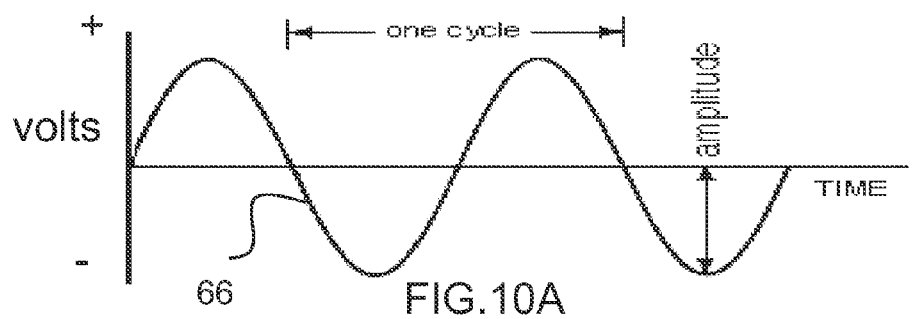
Figure 10B:
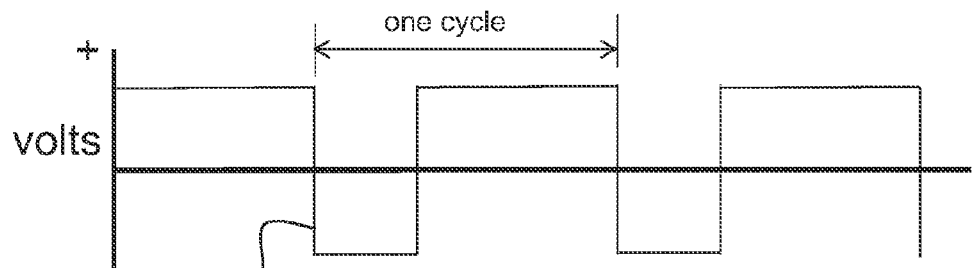
Figure 10C:
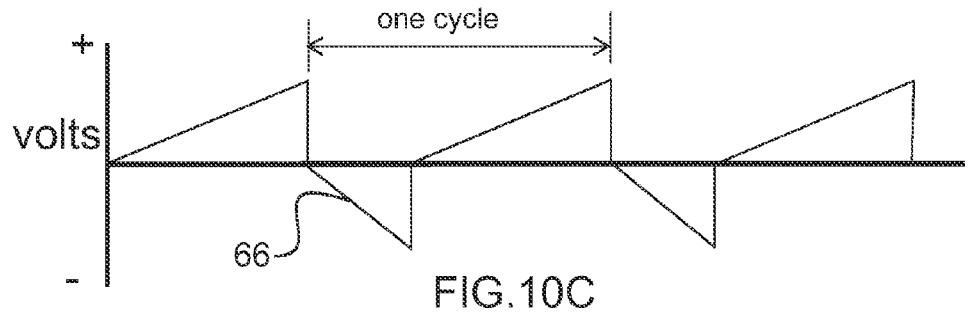
Figure 10D:
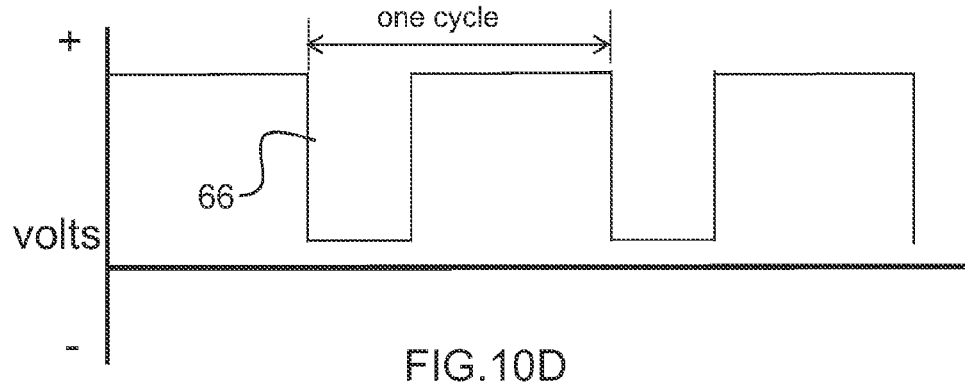

As shown in FIG. 10A through 10D, the electrical stimulating signal 58 may have any suitable profile, such as oscillating as shown in FIG. 10A, periodic as shown in FIG. 10B, and saw-tooth as shown in FIG. 10C. As shown in FIG. 10A, the voltage amplitude moves from positive to negative therein indicating a reverse polarity signal. However, any of the signals shown and described may reside in one polarity. For example, as shown in FIG. 10D, a periodic signal does not change polarity and remains positive throughout the signal profile. Any combination of signal profiles may be used. It should be understood that the shape of the profile may vary as required. For example, the amplitude and frequency of the oscillating signal may be higher or lower as required, and the oscillating signal may be centered over zero volts, or may produce only a positive or negative voltage. The periodic signal may have any combination of voltage levels and durations. As shown in FIG. 10B, the positive voltage has a longer duration than the negative voltage. As shown in FIG. 10C, a saw-tooth profile has a voltage increase portion, a sudden drop in voltage and a voltage decrease portion, and may have any suitable voltage increase and/or decrease slope, and may have any suitable maximum and minimum voltage values. As shown in FIG. 10C, the voltage increase slope is less than the voltage decrease slope, wherein it takes longer for the voltage to reach the maximum level that it takes to reach the minimum value.

Definitions

Discrete cutting feature, as used herein, means that a cutting feature has separate cutting blade(s) and a separate screen from another cutting features.

Shaving surface, as used herein, is the surface of the razor that is pressed against a user's face and typically comprises one or more cutting features.

Activating electrode, as used herein, is an electrode that is charged and transfers electrical energy to a user's skin.

Return electrode, as used herein, is at a lower potential than the activating electrode and returns charge to the electrical stimulator. A return electrode may be a conductive element that acts as a ground for receiving the charge transferred to a user's skin.

Skin contact feature, as used herein, is any electrode that is configured on the shaving surface. In one embodiment, a skin contact feature may comprise a portion of a cutting feature, such as a screen, and in another embodiment comprises an electrically conductive piece of material. A skin contact feature may surround one or more electrodes.

Stimulator setting feature, as used herein, allows a user to change or set any parameter of the electrical stimulating signal, including the voltage, frequency, signal profile, signal mode and the like. Any suitable type of user input device may be used to set one or more of the electrical stimulating signal parameters.

Frequency, as used herein, is the number of repeating electrical stimulating signal cycles per second.

It will be apparent to those skilled in the art that various modifications, combinations and variations can be made in the present invention without departing from the spirit or scope of the invention. Specific embodiment, features and elements described herein may be modified, and/or combined in any suitable manner. Thus, it is intended that the present invention cover the modifications, combinations and variations of this invention provided they come within the scope of the appended claims and their equivalents.

What is claimed is:

1. An article comprising an electric razor comprising:
   a. a plurality of cutting features comprising;
      i. a blade configured to move; and
      ii. a screen configured over said blade;
   wherein the said blade is configured to rotate or reciprocate or
   wherein the said blade and said screen are configured to rotate or reciprocate;
   b. an electrical stimulator comprising:
      i. a power source;
      ii. a first electrode coupled to at least one screen;
      iii. a second electrode configured on the body of the electric razor where it is configured to make contact with a user's hand;
   whereby an electrical current flows between said first electrode and said second electrode; and
      iv. a controller for controlling an electrical stimulating signal frequency and voltage,
   wherein said electrical stimulator is configured to transmit an electrical current between said first electrode and said second electrode, whereby said electrical current passes through a user's skin and thereby effectively causes a hair to stand up, wherein at least one of the said electrodes is an activating electrode and wherein at least one of the said electrodes is a return electrode.

2. The article of claim 1, wherein the electric razor is a three blade razor comprising
   a. three discrete cutting features; and
   b. three discrete screens.

3. The article of claim 2, wherein a first electrode is couple to all three screens.

4. The article of claim 3, wherein all three screens are activating electrodes or return electrodes.

5. The article of claim 1 wherein the second electrode is configured on a cutting surface.

6. The article of claim 1, wherein the power supply comprises an electrical coupling cord.

7. The article of claim 1, wherein the first electrode is an activating electrode.

8. The article of claim 1, wherein the second electrode is an activating electrode.

9. The article of claim 1, wherein the skin contact feature is a screen.

10. The article of claim 1, wherein the skin contact feature is configured substantially around a cutting feature.

11. The article of claim 1, wherein the skin contact feature is configured around the plurality of cutting features.

12. The article of claim 1, wherein an activating electrode is coupled to a first screen, and a return electrode is coupled to a second screen.

13. The article of claim 1, wherein a first activating electrode is coupled to a first screen, and a second activating electrode is coupled to a second screen, and a return electrode is coupled to a skin contact feature.

14. The article of claim 1, further comprising a user stimulator setting feature.

15. The article of claim 14, wherein the user stimulator setting feature comprises a voltage setting feature, whereby a user can set or change the electrical stimulating signal voltage.

16. The article of claim 1, further comprising a user mode feature, whereby a user may select a mode for use, wherein said mode includes; a razor mode, an electrical stimulator mode and a combination mode.

17. The article of claim 1, wherein the controller controls the electrical stimulating signal, whereby at least one electrode alternates between an activating electrode and a return electrode, thereby producing a reverse polarity electrical stimulating signal.

18. The article of claim 1, wherein the electrical stimulating signal comprises a periodic profile.

19. The article of claim 1, wherein the electrical stimulating signal comprises a saw-tooth profile.

20. An article comprising an electric razor comprising:
   a. a plurality of discrete generally circular shaped cutting features comprising;
      i. a blade configured to move; and
      ii. a screen configured over said blade;
   wherein the said blade is configured to rotate or reciprocate or
   wherein the said blade and said screen are configured to rotate or reciprocate;
      iii. an electrical stimulator comprising;
      iv. a first activating electrode coupled to said screen;
      v. a second return electrode configured on the body of the electric razor where it is configured to make contact with a user's hand;
   whereby an electrical current flows between said first electrode and said second electrode; and
      vi. a controller,
   b. a user stimulator setting feature, whereby a user may change the amount of electrical stimulation; and
   c. a user razor setting feature, whereby a user may turn off the razor and use the article as an electrical stimulator;
   wherein said electrical stimulator is configured to transmit an electrical current between said first electrode and said second electrode,
   whereby said electrical current passes through a user's skin and thereby effectively causes a hair to stand up.

* * * * *